US00PP35613P2

(12) United States Plant Patent
Zlesak et al.

(10) Patent No.: US PP35,613 P2
(45) Date of Patent: Jan. 30, 2024

(54) ***HYDRANGEA* PLANT NAMED 'BAIFUL'**

(50) Latin Name: *Hydrangea arborescens*
Varietal Denomination: BAIful

(71) Applicant: Bailey Nurseries Inc., Newport, MN (US)

(72) Inventors: David Charles Zlesak, River Falls, WI (US); Gail Katherine Soens, Woodbury, MN (US)

(73) Assignee: BAILEY NURSERIES INC., Newport, MN (US)

( * ) Notice: Subject to any disclaimer, the term of this patent is extended or adjusted under 35 U.S.C. 154(b) by 0 days.

(21) Appl. No.: 18/139,321

(22) Filed: Apr. 25, 2023

Related U.S. Application Data

(63) Continuation of application No. 63/337,324, filed on May 2, 2022.

(51) Int. Cl.
*A01H 5/02* (2018.01)
*A01H 6/48* (2018.01)

(52) U.S. Cl.
USPC ..... Plt./250
CPC ..... *A01H 6/48* (2018.05)

(58) Field of Classification Search
USPC ..... Plt./250
CPC ..... A01H 6/48; A01H 5/02
See application file for complete search history.

*Primary Examiner* — Keith O. Robinson
(74) *Attorney, Agent, or Firm* — Penny J. Aguirre

(57) ABSTRACT

A new cultivar of *Hydrangea arborescens* plant named 'BAIful' that is characterized by its strong branches, its compact and well-branched plant habit, its abundant and uniform flowering habit over the outer canopy of the plant, its mophead flowerheads that open white in color, mature to green and fade to brown, its age that has good resistance to bacterial leaf spot, and its overwintered liners that if propagated the season before consistently flower the next growing season.

3 Drawing Sheets

Botanical classification: *Hydrangea arborescens*.
Varietal denomination: 'BAIful'.

BACKGROUND OF THE INVENTION

The present invention relates to a new and distinct cultivar of *Hydrangea arborescens* and will be referred to hereafter by its cultivar name, 'BAIful'. 'BAIful' represents a new smooth *Hydrangea*, a perennial shrub grown for landscape use.

'BAIful' was derived from an ongoing breeding program by the Inventors in Cottage Grove, Minnesota. The goal of the breeding program is to create new cultivars of *Hydrangea* with strong stems, abundant blooms, compact and dense plant habits, good winter hardiness, uniform plant habits, resistance to foliar diseases, and ease of propagation and production. 'BAIful' originated from treatment of open-pollinated seedlings of *Hydrangea arborescens* 'Bounty' (not patented) with trifluralin as a mutagen in 2015. Trifluralin was used to increase genetic variability within the population. Trifluralin can alter plant genetics not only due to hindering spindle fibers during cell division and leading to polyploidization, but also, like other dinitroaniline herbicides (trifluralin and oryzalin are the most popular), can contribute to unpredictable mutations, even when cells maintain the original ploidy level. The male parent of 'BAIful' is unknown. The trifluralin-treated seedlings that resulted were highly variable in characteristics, however, 'BAIful' was clearly unique. 'BAIful' had characteristics outside of the typical characteristics associated with polyploidization and that are routinely found in seedling populations of *Hydrangea arborescens*.

Asexual propagation of the new cultivar was first accomplished by softwood stem cuttings by one of the Inventors in summer of 2016 in Cottage Grove, Minnesota. Asexual propagation by softwood, semi-hardwood, and hardwood stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'BAIful' as a unique cultivar of *Hydrangea arborescens*.

1. 'BAIful' exhibits strong branches.
2. 'BAIful' exhibits a compact and well-branched plant habit.
3. 'BAIful' exhibits abundant and uniform flowering habit over the outer canopy of the plant.
4. 'BAIful' exhibits mophead flowerheads that open white in color, mature to green and fade to brown.
5. 'BAIful' exhibits foliage that has good resistance to bacterial leaf diseases.
6. 'BAIful' exhibits overwintered liners that if propagated the season before consistently flower the next growing season.

The known maternal parent of 'BAIful' differs from 'BAIful' in having a less compact plant habit, less branching, a later blooming period that blooms less freely, weaker stems that are prone to splaying and bending in wind and storms, and leaves that are larger in size and less uniform in shape and color. 'BAIful' can also be most compared to *Hydrangea arborescens* cultivars 'Abetwo' (U.S. Plant Pat.

No. 20,571) and 'Annabelle' (not patented). 'Abetwo' and 'Annabelle' are both similar to 'BAIful' in having flowers that open white in color, maturing to green in color and then fade to brown in color, and in commencing bloom at a similar time on mature plants in the landscape. 'Abetwo' and 'Annabelle' both differ from 'BAIful' in having flowers that are larger in size, a less floriferous blooming habit, a less compact and less dense plant habit, and in being prone to stems bending and falling due to wind and storms. It should be noted that typical phenotypic characteristics associated with polyploidization (e.g. less branching, more brittle stems, and larger and thicker plant organs) have not been observed in 'BAIful' (polyploidization is one possible outcome of treatment with trifluralin). Measurement of leaf guard cell size suggests that 'BAIful' is likely not polyploid. It is unclear to what extent or how trifluralin may have altered the genetics of 'BAIful' and contributed to the unique combination of traits in 'BAIful'. These unique traits (not described in the literature as predictable or typical outcomes of trifluralin) include uniform flowering over the canopy, a dense and well-branched plant habit, abundant flowering, good resistance to bacterial leaf diseases, and overwintered liners consistently blooming the next season.

BRIEF DESCRIPTION OF THE DRAWINGS

The accompanying color photographs illustrate the overall appearance and distinct characteristics of the new *Hydrangea*. The photographs were taken of a plant six years in age as grown outdoors in a trial plot in Cottage Grove, Minnesota.

The photograph in FIG. 1 provides a view of the plant habit of 'BAIful' in bloom.

Figure 1:
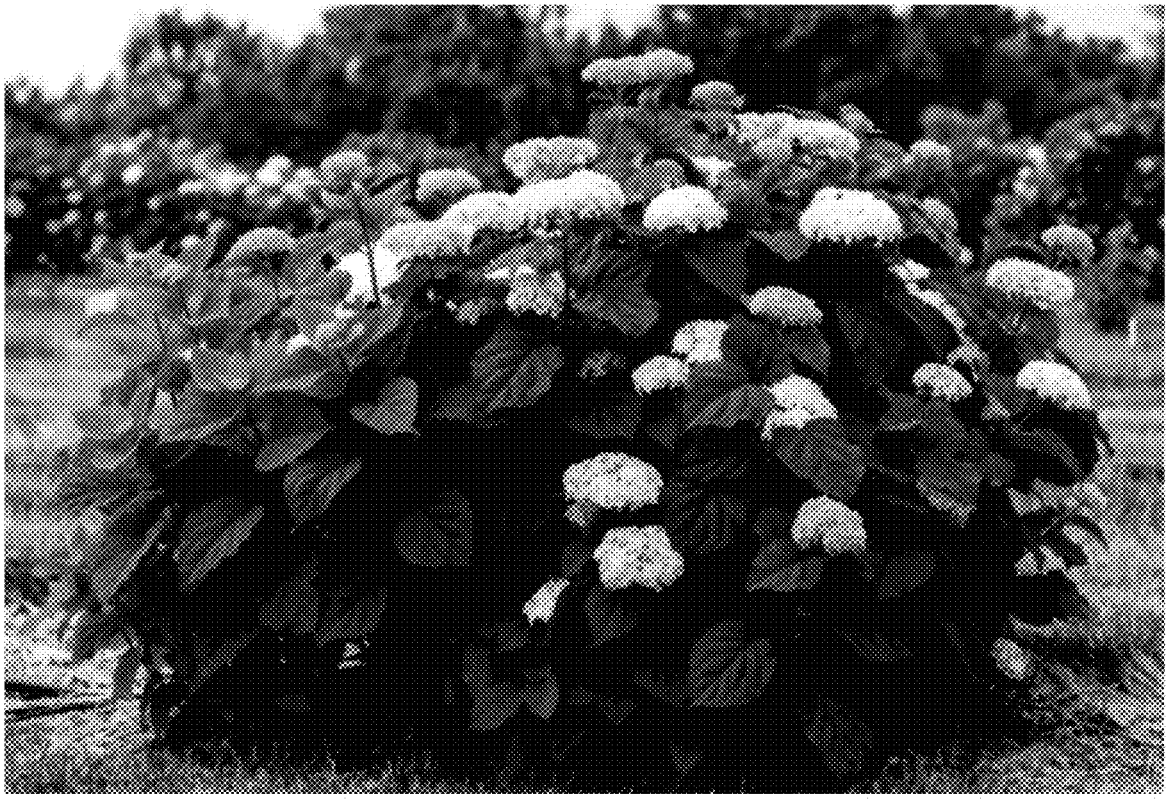
Figure 2:
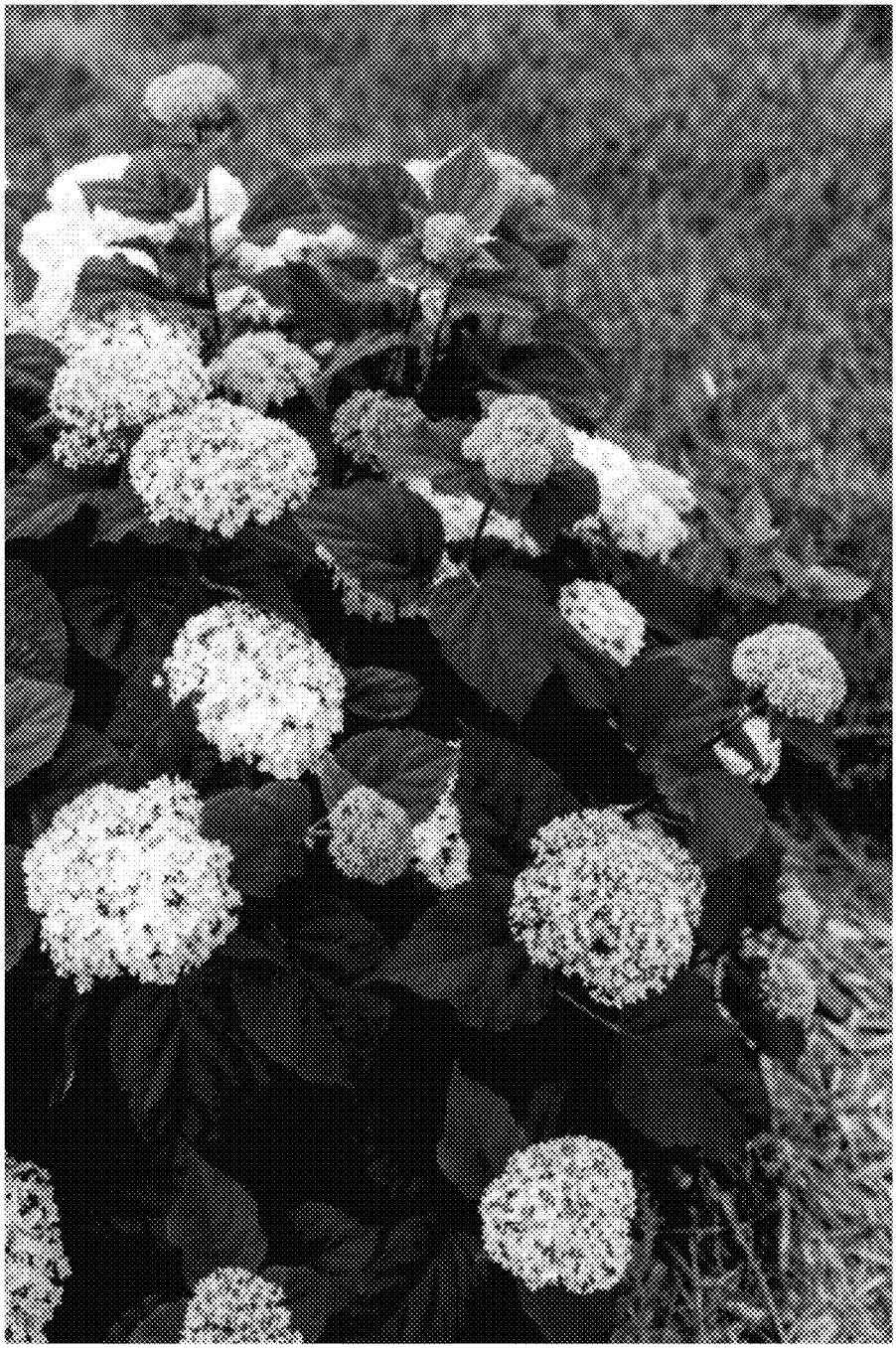

The photograph in FIG. 2 provides a close-up view of the inflorescences of 'BAIful'.

Figure 3:
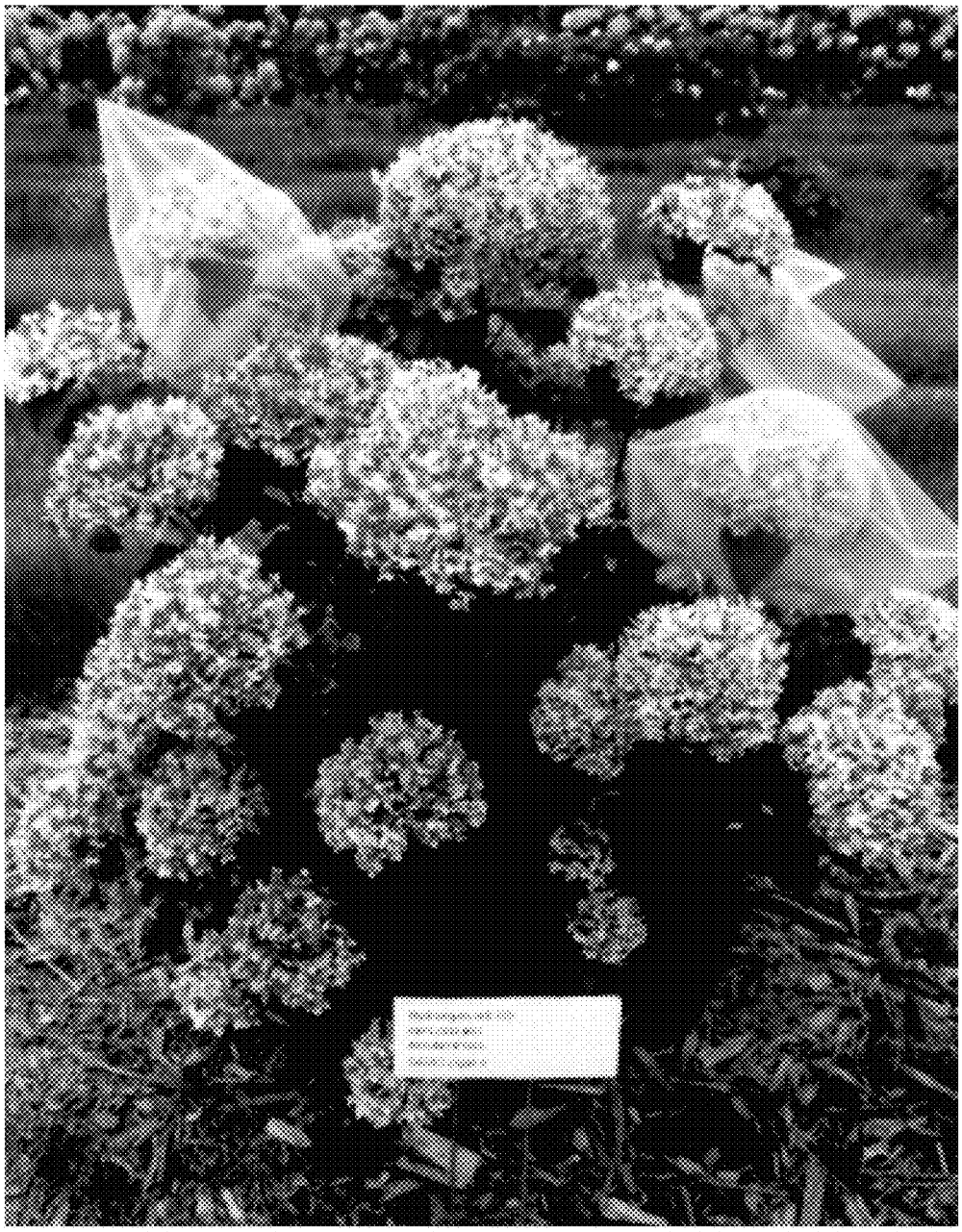

The photograph in FIG. 3 provides a view of the inflorescences of 'BAIful' when maturing.

The colors in the photographs are as close as possible with the photographic and printing technology utilized and the color values cited in the detailed botanical description accurately describe the colors of the new *Hydrangea*.

BOTANICAL DESCRIPTION OF THE PLANT

The following is a detailed description of plants two years in age as grown outdoors in 2-gallon containers in Cottage Grove, Minnesota and in a garden in River Falls, Wisconsin with the capsule description taken from a 6-year-old plant that was field grown in Cottage Grove, Minnesota. The phenotype of the new cultivar may vary with variations in environmental, climatic, and cultural conditions, as it has not been tested under all possible environmental conditions. The color determination is in accordance with the 2015 Colour Chart of The Royal Horticultural Society, London, England, except where general color terms of ordinary dictionary significance are used.

General description:

- *Blooming period.*—From mid-June through mid-July for main flush with some continued flowering possible to fall in Minnesota.
- *Plant type.*—Perennial shrub with mophead-like flowerheads.
- *Plant habit.*—Sturdy and straight stems, rounded, compact in shape.
- *Height and spread.*—Reaches 86 cm in height and 1 m in spread as a 4-year-old plant in the landscape.
- *Cold hardiness.*—At least to U.S.D.A. Zone 4.
- *Diseases and pests.*—Resistance to bacterial leaf spot caused by *Xanthomonas campestris*.
- *Root description.*—Fibrous.
- *Time required for root development.*—2 weeks for root initiation, 6 weeks to produce a fully rooted plug.
- *Growth rate.*—Vigorous.

Stem description:

- *Stem shape.*—Rounded.
- *Stem strength.*—Strong, do not lodge.
- *Stem aspect.*—Upright to slightly outward.
- *Stem color.*—Young; 142A, heavily flushed with 183A, mature and older bark; 142B with vertical striations of 183A.
- *Stem size.*—An average of 50 cm (excluding the inflorescence) in length and 5 mm in diameter.
- *Stem surface.*—Young; both surfaces dull and densely tomentose with soft matted hairs, slightly translucent and 196B, too small to measure size, mature; glabrous and slightly glossy.
- *Branching.*—Freely branched with an average of 35 lateral branches.
- *Internode length.*—An average of 8 cm.

Foliage description:

- *Leaf shape.*—Ovate to broadly ovate.
- *Leaf arrangement.*—Opposite.
- *Leaf division.*—Simple.
- *Leaf number.*—An average of 12 per lateral branch.
- *Leaf base.*—Cordate.
- *Leaf apex.*—Apiculate.
- *Leaf margins.*—Dentate to serrate.
- *Leaf venation.*—Pinnate, upper surface slightly translucent and 149A in color, lower surface 138C, densely tomentose with soft matted hairs that match leaf surface and too small to measure size.
- *Leaf size.*—An average of 7 cm in length, 6 cm in width.
- *Leaf attachment.*—Petiolate.
- *Leaf surface.*—Upper surface; dull and slightly rugose, lower surface; moderately rugose, upper surface moderately covered with short stiff hairs, 0.3 mm in length, NN155D in color, lower surface densely tomentose with soft matted hairs that match leaf surface and too small to measure size.
- *Leaf color.*—Young and mature; upper surface 143A, slightly flushed with 141A, lower surface 138C.
- *Petioles.*—An average of 4 cm in length and 3 mm in diameter, 142A, heavily flushed with 183A, both surfaces dull and densely tomentose with soft matted hairs, slightly translucent and 196B, too small to measure size.

Inflorescence description:

- *Inflorescence type.*—Round, flattened, mophead, compound corymb of rotate-shaped sterile flowers over fertile flowers.
- *Lastingness of inflorescence.*—Sterile and fertile flowers; an average of 4 weeks, sterile flowers persistent, fertile flowers self-cleaning.
- *Inflorescence number.*—One per lateral stem.
- *Inflorescence size.*—An average of 5 cm in depth and 15 cm in diameter.
- *Flower number.*—An average of 500 sterile flowers and 250 fertile flower buds per inflorescence.
- *Flower fragrance.*—Light, sweet scent.

*Flower aspect.*—Sterile flowers; upright, outwards and slightly drooping, fertile flowers; upright.

*Flower size.*—Sterile flowers; an average of 1.3 cm in diameter and 4 mm in depth, fertile flowers; an average of 1.0 cm in diameter and 5 mm in depth.

*Flower shape.*—Sterile flowers; rotate, fertile flowers; rotate.

*Flower buds.*—Sterile flowers; 2.3 mm in diameter, 2 mm in depth, rounded and flattened, color; young 149A, mature 157D, fertile flowers; 2 mm in diameter and depth, rounded in shape, color; young 150B, mature 157D.

*Peduncles.*—An average of 3 cm in length and 3 mm in diameter, held upright, moderately strong, 142A, heavily flushed with 183A, both surfaces dull and densely tomentose with soft matted hairs, slightly translucent and 196B, too small to measure size.

*Pedicels.*—Sterile and fertile flowers; average of 10 to 12 mm in length, 1 mm in diameter and 2 to 6 mm in length and 0.5 mm in diameter, respectively, pedicels of both kinds of flowers are moderately strong, held in multiple angles outwards from vertical, 142C in color, dull surface that is densely tomentose with soft matted hairs matching surface color.

*Petals.*—Sterile flowers; 3 to 4, elliptic in shape, acute margins, cuneate base, concave in aspect, 0.5 mm in length, 0.3 mm in width, color; young 150B, mature 157D, fertile flowers; 5, elliptic in shape, acute margins, cuneate base, concave in aspect, 2 mm in length, 1 mm in width, color; young 150B, mature 157D.

*Sepals.*—Sterile flowers; an average of 3 to 4, rotate in arrangement, ovate in shape, very slightly concave, very short apiculate apex, cuneate base, entire margin, an average of 7 mm in length and 6 mm in width, color; upper and lower surface when opening 149A, upper and lower surface when fully open 157D, both surfaces; glabrous, smooth, velvety, fertile flowers; rotate in arrangement, angled upward, flat, deltoid in shape, truncate base, acute apex, entire margin, an average of 1 mm in length and 1 mm in width, color: upper and lower surface when opening 142C and mature also 142C on both surfaces.

Reproductive organs:

*Gynoecium.*—Sterile; none observed, fertile flowers; perigynous, compound pistil with two or rarely three carpels per flower, an average of 2.5 mm in length, stigmas separate and are club shaped 1.0 mm in length and 0.5 mm in diameter and are angled outward from each other, 155C in color, style 0.5 mm in length and 0.5 mm in diameter, 155C in color, ovary globular and 1.5 mm in length and width, color 154D.

*Androecium.*—Sterile; typically none observed, but periodically 3-5 stamens, filaments 3 to 4 mm in length and 0.3 mm in diameter, color 155C, anthers 0.5 mm in length and width, color 160C, pollen sparce, color NN155B, fertile flowers; 10 stamens, filaments 3 to 5 mm in length and 0.3 mm in diameter, color 155C, anthers 0.5 mm in length and width, color 160C, pollen moderate, color NN155B.

*Fruit and seed.*—Capsules; generally globular in shape with persistent sepals and stigmas, 2 to 3 mm in length and width, color at maturity 165A, seeds; abundant and small, 1 mm in length and 0.15 mm in width, color, 164A.

It is claimed:

1. A new and distinct cultivar of *Hydrangea* plant named 'BAIful' substantially as herein illustrated and described.

* * * * *